United States Patent [19]
Verkaart

[11] Patent Number: 5,512,043
[45] Date of Patent: Apr. 30, 1996

[54] NEEDLELESS INJECTION SITE

[75] Inventor: Wesley H. Verkaart, Duxbury, Mass.

[73] Assignee: Level 1 Technologies, Rockland, Mass.

[21] Appl. No.: 205,259

[22] Filed: Mar. 3, 1994

[51] Int. Cl.$^6$ ............................................. A61M 37/00
[52] U.S. Cl. ........................ 604/83; 137/853; 251/4; 604/247
[58] Field of Search ................................ 604/246, 247, 604/249, 83; 137/605, 853; 251/61.1, 4

[56] References Cited

U.S. PATENT DOCUMENTS

| | | | |
|---|---|---|---|
| 1,094,685 | 4/1914 | Spangler . | |
| 2,770,234 | 11/1956 | Nesset et al. . | |
| 3,057,350 | 10/1962 | Cowley . | |
| 3,085,549 | 4/1963 | Kacsuta . | |
| 3,307,571 | 3/1967 | Smith . | |
| 3,416,567 | 12/1968 | Von Darder | 604/83 |
| 3,994,293 | 11/1976 | Ferro . | |
| 4,063,555 | 12/1977 | Ulinder . | |
| 4,502,502 | 3/1985 | Krug | 137/512.3 |
| 4,666,427 | 5/1987 | Larsson et al. | 604/51 |
| 4,666,429 | 5/1987 | Stone | 604/83 |
| 4,774,940 | 10/1988 | Linder | 128/204.18 |
| 4,819,684 | 4/1989 | Zaugg et al. | 604/247 |
| 4,871,356 | 10/1989 | Haindl et al. | 604/247 |
| 4,908,018 | 3/1990 | Thomsen | 604/247 |
| 5,041,087 | 8/1991 | Loo et al. | 604/247 |
| 5,098,405 | 3/1992 | Peterson et al. | 604/247 |

*Primary Examiner*—John G. Weiss
*Attorney, Agent, or Firm*—Dickinson, Wright, Moon, Van Dusen & Freeman

[57] ABSTRACT

An injection site designed for use with a needleless syringe includes a housing placed in an infusion line and an inlet for engaging the syringe and conveying a fluid to be mixed with the infusate to the interior of the housing. A liner within the housing controls flow of fluid through the inlet by sealing the inlet when the pressure in the housing is equal to or exceeds the pressure in the syringe. The housing is made of two parts, each of which includes a flange. When assembled, the spaced flanges are on opposite ends of the liner, which is not directly attached to the housing, to limit movement of the liner to maintain its position in the housing.

10 Claims, 2 Drawing Sheets

NEEDLELESS INJECTION SITE

TECHNICAL FIELD

This invention relates to the art of devices for supply of physiological fluids. In particular, the invention facilitates introduction of fluids into an intravenous line without requiring the use of an injection needle.

BACKGROUND

It is often necessary to introduce a secondary fluid, such as medication, into a fluid that is being supplied to a patient intravenously. Several devices are known for this purpose. One category of such devices uses a membrane that is designed to be pierced by a hypodermic needle. Because of the dangers associated with sharp objects that can injure healthcare workers, however, injection sites that do not require the use of needles are more desirable.

One such device is shown in U.S. Pat. No. 3,416,567 (Von Dardel et al.) where a resilient sleeve seals a feed-in orifice until the pressure of the secondary fluid is large enough to push the sleeve away from the orifice to allow the secondary fluid to enter the stream of the primary fluid. A device of similar construction is shown in U.S. Pat. No. 3,085,549 (Kacsuta).

SUMMARY OF THE INVENTION

These known devices are of complicated constructions and require complex manufacturing steps. The Von Dardel device, for example, requires the resilient sleeve to be secured to an upstream end of the valve and the downstream end to be free to deform to allow the secondary fluid to enter the fluid stream. Moreover, the mixing provided by such devices may be inadequate because the fluid to be mixed engages the primary fluid only at the downstream portion of the sleeve.

In accordance with the invention, a needleless injection site includes a relatively rigid cylindrical housing and a resilient liner. The housing has an inlet for the primary fluid, an inlet for the secondary fluid, and an outlet for the two, mixed fluids. The inlet for the primary fluid and the outlet communicate freely with an interior space formed by the liner. The secondary fluid, however, is supplied through an opening in the housing adjacent an exterior surface of the liner.

The outer diameter of the liner is slightly larger than the inner diameter of the housing, whereby the liner is held tightly against the inner surface of the housing when the pressure in the interior space of the housing is larger than the pressure on the outer surface of the liner. Thus, the liner provides a seal against the opening for the secondary fluid unless the pressure of the secondary fluid is greater than the pressure of the primary fluid.

When the pressure of the secondary fluid exceeds that of the primary fluid, the secondary fluid pushes the liner away from the opening for the secondary fluid to allow the secondary fluid to flow into the space between the liner and the housing, around either or both ends of the liner, and into the interior space to mix with the primary fluid.

The liner is not attached to the housing and is held in alignment with the outer section by two longitudinally spaced flanges on the housing. These flanges bracket the liner and permit some longitudinal variation in position of the liner, precise positioning being unnecessary for operation of the device. Proper sealing of the liner against the housing is provided by precise control of the outer diameter of the liner and the inner diameter of the housing. This control is easily attained with known manufacturing techniques.

For ease of assembly, the housing is preferably made of two injection-molded parts. A first of the parts includes a cylindrical portion, one of the flanges, and an outlet (or inlet). The other of the parts includes the other of the flanges and the inlet (or outlet). The resilient liner is an extruded element that has been cut to the desired length. During assembly, the inner element is placed in the cylindrical portion of the first of the two parts, and the second of the parts is then secured to the first part by known techniques, such as ultrasonic welding.

By the above construction, a needle-less injection site is easily manufactured because the important dimensions are easily controlled, and dimensions that are not easily controlled are made unimportant to the operation of the device.

DETAILED DESCRIPTION OF THE PREFERRED EMBODIMENT

Figure 1:
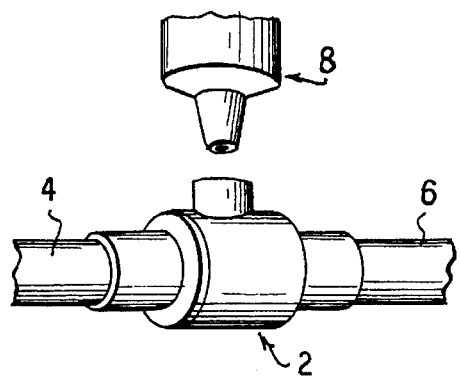
FIG. 1 is a perspective of a needleless injection site in accordance with the invention.
Figure 2:
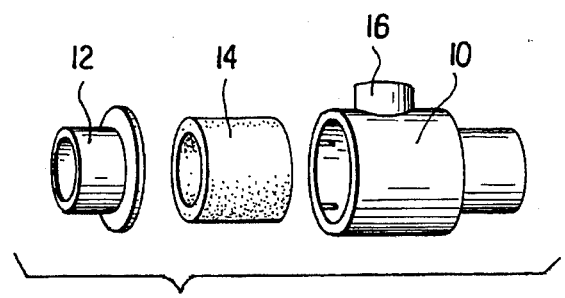
FIG. 2 is an exploded view of the injection site shown in FIG. 1.

With reference to FIG. 1, a needleless injection site 2 is located in an infusion line including a first segment 4 and a second segment 6. The injection site is designed for mixing fluids flowing in the infusion line with fluids received from a needleless syringe 8.

Figure 3:
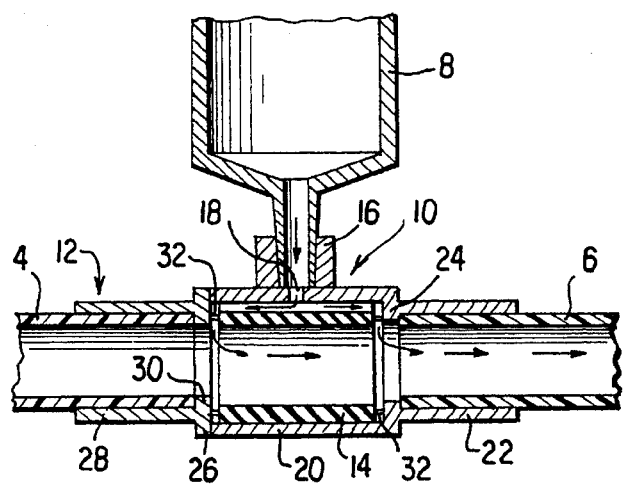
FIG. 3 is a longitudinal cross section of the injection site of FIG. 1.
Figure 4:
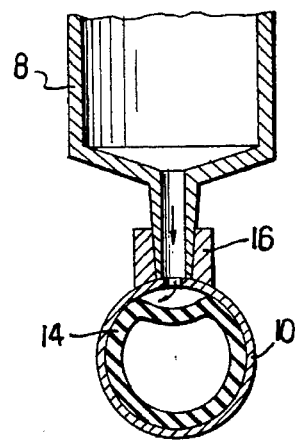
FIG. 4 is a transverse cross section of the injection site of FIG. 1 showing the injection of a secondary fluid.
Figure 5:
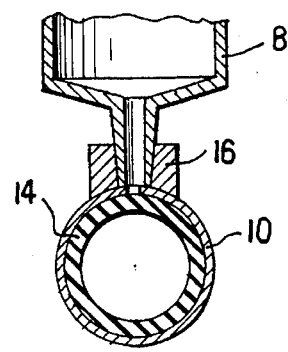
FIG. 5 is a transverse cross section of the injection site of FIG. 1 showing the injection site in a sealed condition.

The components of the injection site according to the invention will be described with reference to FIGS. 2 through 5. The injection site generally includes a housing portion 10, a cap portion 12, and a liner 14 that fits within the housing. The housing includes a receptacle 16 for engaging the tip of the syringe 8, and the receptacle communicates with the interior of the housing by way of an opening 18. Liner 14 is a cylinder made of elastomeric material, the outer diameter of the cylinder being slightly larger than the inside diameter of the housing 10. Thus, the liner is naturally urged against the inside of the housing to seal the opening 18, as illustrated in FIG. 5, in the absence of fluid pressure applied to opening 18, for example by the syringe. When fluid pressure is applied, the liner is pushed away from the interior of the housing, and the secondary fluid flows into the housing between the liner and the housing and then around the ends of the liner to mix with the fluid flowing in the infusion line. The condition where the liner has been pushed away from sealing contact with the housing to allow introduction of the secondary fluid is illustrated in FIGS. 3 and 4.

The construction of the housing 10 and the cap 12 is such that the liner is held in the correct longitudinal position without being attached to the housing. Thus, the housing has a larger, cylindrical portion 20 for receiving the liner, a smaller portion 22 for receiving the infusion line 6, and a flange 24 between these portions. Similarly, cap 12 includes an outer portion 26 for engaging the cylindrical portion 20 of the housing, a smaller portion 28 for receiving the infusion line, and a flange 30 extending radially inward. The flanges 24 and 30 extend radially inward by a distance adequate to engage the ends of the liner to limit the longitudinal movement of the liner with respect to the housing and maintain it in the proper location with respect to the opening 18.

The flanges may alternatively be provided with protuberances 32 that extend longitudinally to prevent sealing engagement between the end surfaces of the liner and the flanges. This ensures the presence of a gap between the ends of the liner and the flanges through which the fluid can flow, over the ends of the liner, into the infusate stream.

Figure 6A:
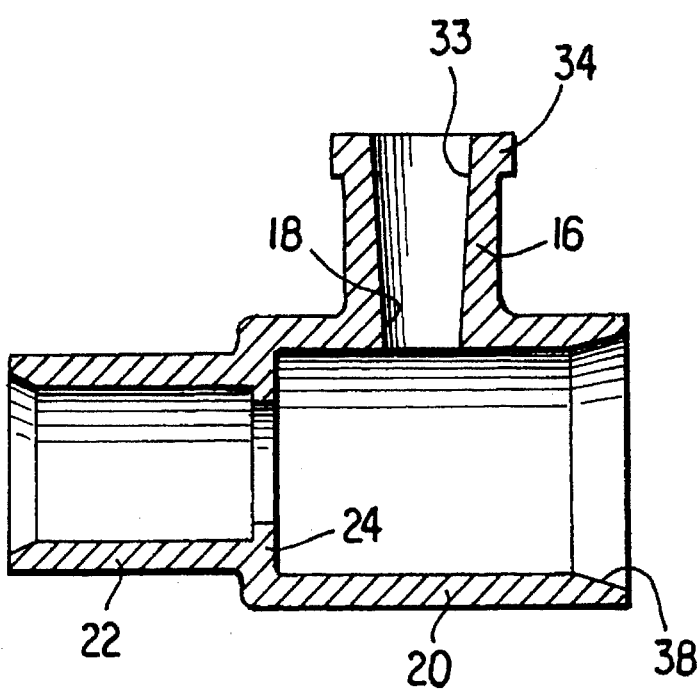
FIG. 6a is a transverse cross section of the housing portion of a preferred embodiment of the invention.
Figure 6B:
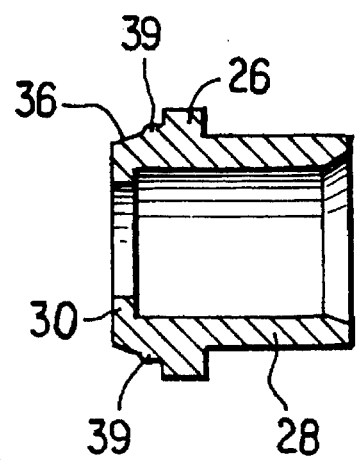
FIG. 6b is a transverse cross section of the cap portion of a preferred embodiment of the invention.

FIGS. 6a and 6b, respectively, show a preferred embodiment of the housing and cap portions of the invention. As shown in FIG. 6a, the receptacle 16 includes both a tapered channel 33 for receiving a syringe and a luer lock thread 34 for receiving separately a luer connector attached to a fluid inlet line (not shown). The end of the cylindrical portion 20 is tapered at 38 for matching a tapered portion 36 on the end of the cap. Thus, during assembly, the two parts are easily engaged together after insertion of the liner. These parts may be attached together by any of several known techniques, one preferred technique being ultrasonic welding. The tapered part of the cap portion is also preferably provided with a small annular wedge 38 that melts during the ultrasonically welding to cement the parts together.

While the injection site of the invention is primarily designed for use with a needleless syringe, the liner is nevertheless capable of being pierced by a needle to permit injection of fluids with a hypodermic syringe, should the need arise. In this regard, the symmetrical arrangement of the liner between the flanges ensures that the pressure of the needle is evenly applied.

It will be appreciated that a versatile injection site has been shown and described. The housing and cap portions are injection molded, the inside diameter of the housing having small tolerances. The liner is cut from an extruded tube, the exterior diameter being subject to small tolerances. The device is then assembled by placing the liner in the housing, applying the cap, and welding the cap and housing together. Modifications within the scope of the appended claims will be apparent to those of skill in the art.

I claim:

1. Apparatus for mixing a first fluid with a second fluid comprising a housing having a first inlet for receiving said first fluid, a second inlet for receiving said second fluid, and an outlet for dispensing said first and second fluids, sealing means for sealing said second inlet when the fluid pressure of said first fluid is equal to or exceeds the fluid pressure of said second fluid, and means for maintaining the axial position of said sealing means within said housing, wherein said sealing means comprising an elastic element capable of deforming radially inwardly along its entire length and is separate from and not attached to said housing, whereby said second fluid can pass over opposed ends of said sealing means during mixing.

2. Apparatus according to claim 1 wherein said housing further comprises retaining means for retaining said sealing means in said housing.

3. Apparatus according to claim 2 wherein said retaining means comprises at least one flange for engaging said sealing means.

4. Apparatus according to claim 3 wherein said housing is cylindrical and said sealing means is cylindrical and coaxial with said housing.

5. Apparatus according to claim 4 wherein said first inlet and said outlet are aligned with the cylindrical axis of said housing.

6. Apparatus according to claim 3 wherein said retaining means comprises spaced flanges on opposite ends of said sealing means.

7. A needleless injection site comprising housing means forming a cavity, said housing means having a first fluid inlet to said cavity, a fluid outlet from said cavity, and a second fluid inlet to said cavity, a liner in said cavity for resiliently engaging said second fluid inlet and controlling the flow of said second fluid into said cavity, wherein said liner is not attached to said housing, is maintained in position by spaced flanges at opposite ends of said cavity, and is capable of deforming radially inwardly along its entire length, whereby said second fluid can pass over ends of said liner.

8. An injection site according to claim 7 wherein said cavity is generally cylindrical and said second fluid inlet is in an outer wall of said housing, said liner is generally cylindrical, and said flanges extend radially inward from said outer wall of said housing.

9. An injection site according to claim 8 wherein said housing means comprises a first housing portion and a cap portion secured together, said housing portion including said outer wall.

10. An injection site for facilitating injection of an injected fluid into a flowing fluid comprising a housing having an injection port for admitting said injected fluid to said flowing fluid and a flexible liner for covering said injection port when said injected is not injected and moving away from said injection port when said fluid is injected to permit passage of said fluid through said injection port, wherein said housing comprises axially spaced positioning means for positioning said liner and said liner is capable of deforming radially inwardly along its entire length is detached from said housing, and is located between said positioning means for maintaining the axial position of said liner, whereby said injected fluid can pass over opposed ends of said liner for mixing with said flowing fluid.

* * * * *